(12) United States Patent
Hou et al.

(10) Patent No.: US 11,576,633 B2
(45) Date of Patent: Feb. 14, 2023

(54) COLLIMATOR FOR DETECTOR AND APPLICATION THEREOF

(71) Applicant: BEIJING NOVEL MEDICAL EQUIPMENT LTD., Beijing (CN)

(72) Inventors: Yansong Hou, Beijing (CN); Haipeng Wang, Beijing (CN); Lilei Gao, Beijing (CN); Tianpeng Xu, Beijing (CN); Dongling Tian, Beijing (CN); Nianming Jiang, Beijing (CN); Chang Qi, Beijing (CN); Mai Liu, Beijing (CN)

(73) Assignee: BEIJING NOVEL MEDICAL EQUIPMENT LTD., Beijing (CN)

( * ) Notice: Subject to any disclaimer, the term of this patent is extended or adjusted under 35 U.S.C. 154(b) by 86 days.

(21) Appl. No.: 17/052,305

(22) PCT Filed: May 6, 2019

(86) PCT No.: PCT/CN2019/085728
§ 371 (c)(1),
(2) Date: Apr. 26, 2021

(87) PCT Pub. No.: WO2019/210883
PCT Pub. Date: Nov. 7, 2019

(65) Prior Publication Data
US 2021/0236071 A1 Aug. 5, 2021

(30) Foreign Application Priority Data

May 2, 2018 (CN) .......................... 201810409873.6
May 2, 2018 (CN) .......................... 201820647942.2

(51) Int. Cl.
*A61B 6/00* (2006.01)
*A61B 6/03* (2006.01)
*G02B 27/30* (2006.01)

(52) U.S. Cl.
CPC .............. *A61B 6/405* (2013.01); *A61B 6/037* (2013.01); *G02B 27/30* (2013.01)

(58) Field of Classification Search
None
See application file for complete search history.

(56) References Cited

U.S. PATENT DOCUMENTS

2004/0232348 A1\* 11/2004 Beekman .............. G01T 1/2985
250/393

FOREIGN PATENT DOCUMENTS

CN 105232074 1/2016
JP 2001503508 A 3/2001

OTHER PUBLICATIONS

WIPO, ISR for PCT/CN2019/085728, Jul. 26, 2019.
(Continued)

*Primary Examiner* — Edwin C Gunberg
(74) *Attorney, Agent, or Firm* — Hodgson Russ LLP (57) ABSTRACT

A collimator for a detector is disclosed. The collimator comprises: a bottom plate provided with imaging through holes distributed in an array, each of the imaging through holes comprising a first hole segment and a second hole segment, the transverse size of the first hole segment gradually decreasing in a direction from a free end to the second hole segment, and the transverse size of the second hole segment gradually decreasing in a direction from the free end to the first hole segment; a shielding case formed on the bottom plate; and a top plate disposed in the shielding case and closing at least a part of an opening of the shielding case, the top plate being provided with shielding through holes distributed in an array, and the imaging through holes being in one-to-one correspondence with the shielding through holes.

19 Claims, 5 Drawing Sheets

(56) References Cited

OTHER PUBLICATIONS

EPO, Search Report issued for EP Application No. 19797148.4, dated Jan. 5, 2022.
JPO, Notice of Reasons for Refusal issued for JP Application No. 2021-510513, dated Nov. 24, 2021.

\* cited by examiner

FIG. 11

COLLIMATOR FOR DETECTOR AND APPLICATION THEREOF

CROSS-REFERENCE TO RELATED APPLICATIONS

This application is a national phase entry under 35 USC § 371 of International Application PCT/CN2019/085728, filed May 6, 2019, which claims priority to Chinese Patent Application No. 201810409873.6, titled "COLLIMATOR FOR DETECTOR AND APPLICATION THEREOF" and Chinese Patent Application No. 201820647942.2, titled "COLLIMATOR FOR DETECTOR AND DETECTOR HAVING THE SAME", both of which are filed with CNIPA on May 2, 2018, the entire contents of which are incorporated herein by reference.

TECHNICAL FIELD

This application relates to the field of nuclear medical imaging technology, particularly to a collimator for a detector and the application thereof, and more particularly to a collimator for a detector and a detector.

BACKGROUND

Emission tomography is a non-invasive nuclear medical imaging method. Single Photon Emission Computed Tomography (SPECT) is a type of emission tomography and has been widely used in pre-clinical drug research and clinical disease diagnosis. Spatial resolution and detection efficiency are two important technical indicators of measuring the imaging performance of SPECT. SPECT imaging needs to collimate rays and often uses parallel-hole collimators in traditional clinical practice. With the development of nuclear medicine, the spatial resolution and detection efficiency of SPECT using the parallel-hole collimators cannot meet higher clinical requirements. For imaging of small organs, such as heart, thyroid, brain and the like, if traditional SPECT detectors are equipped with special multi-pinhole collimator, higher detection efficiency and better spatial resolution can be achieved by narrowing an imaging field of view and designing suitable magnification and arrangement of the pinholes. Therefore, the multi-pinhole SPECT imaging system is currently an important trend for the development of emission tomography.

However, the clinical application of multi-pinhole collimators still needs to overcome some difficulties. Although the multi-pinhole collimator has a field of view targeted at a small human organ, radioactive rays from other parts of the human body may also generate projections on the detector through the pinholes, and if these projections overlap with a projection of the small organ, the reconstructed spatial resolution will be reduced or it will be difficult to reconstruct a reasonable image. In order to obtain higher detection efficiency, the pinholes of the multi-pinhole collimator need to be designed with a relatively large diameter, in which case the overlap of projections will be aggravated due to the influence of a penumbra region of pinhole projections. By increasing the thickness of a collimator plate, the penumbra region can be reduced to a certain extent, but the excessive thickness of collimators increases the material cost and the processing difficulty, which cannot be applied in practice.

Therefore, it is desirable to develop a collimator that can effectively eliminate the overlap of different pinhole projections in the multi-pinhole collimators and take into account detection efficiency, spatial resolution, and reconstructed image quality.

SUMMARY

The present disclosure aims to solve at least one of the problems existing in the related art. Accordingly, an objective of the present disclosure is to propose a collimator for a detector, and the collimator uses a top plate to secondarily shield radioactive rays passing through imaging through holes, so as to reduce the overlap between different pinhole projections and improve the detection efficiency and spatial resolution of the detector significantly, thereby resulting in better quality of reconstructed images.

In an aspect of the present disclosure, a collimator for a detector is provided. According to embodiments of the present disclosure, the collimator includes: a bottom plate provided with imaging through holes distributed in an array, wherein the imaging through hole includes a first hole segment and a second hole segment, wherein a transverse size of the first hole segment gradually decreases from a free end to the second hole segment, and a transverse size of the second hole segment gradually decreases from a free end to the first hole segment; a shielding case formed on the bottom plate; and a top plate arranged in the shielding case and closing at least a part of an opening of the shielding case, wherein the top plate is provided with shielding through holes distributed in an array, and the imaging through holes and the shielding through holes are arranged in one-to-one correspondence.

The collimator according to embodiments of the present disclosure can reduce the overlap between different pinhole projections by using a top plate to secondarily shield radioactive rays passing through imaging through holes, and can change a ratio of a light-shielding rate by adjusting a distance between the top plate and a bottom plate and parameters of an imaging through hole and a shielding through hole. Hence, the detection efficiency and spatial resolution of an imaging system of the detector can be improved significantly, and better quality of reconstructed images can be achieved. Additionally, the collimator has low processing cost and can be popularized and applied widely.

In addition, the collimator according to the embodiments of the present disclosure can have the following technical features.

According to an embodiment of the present disclosure, the first hole segment and the second hole segment are symmetrically arranged in an up-down direction.

According to an embodiment of the present disclosure, the first hole segment and the second hole segment are independently configured into a truncated cone or a truncated polygonal pyramid.

According to an embodiment of the present disclosure, the shielding through hole is a straight hole or an oblique hole.

According to an embodiment of the present disclosure, a lower edge of the shielding through hole coincides with an intersection line between an extension surface of a peripheral surface where an inner wall of the first hole segment is located and a lower surface of the top plate.

According to an embodiment of the present disclosure, the collimator has a light-shielding rate of less than 100%, wherein the light-shielding rate is determined by the formula:

$$\text{Light-shielding rate} = \frac{S_1}{S_2} = \left( \frac{H \tan\frac{\alpha}{2} + \frac{HD}{T} - \frac{D}{2}}{H \tan\frac{\alpha}{2} + \frac{D}{2}} \right)^2 - 1$$

in which $S_1$ represents a projected area of a penumbra region of the collimator; $S_2$ represents a projected area of an umbra region of the collimator; H represents a distance from a center of the imaging through hole to a surface of the detector; a represents an included angle from a midpoint of a connecting surface of the first hole segment and the second hole segment to the free end of the first hole segment; D represents a maximum diameter of the imaging through hole; T represents a distance from a bottom surface of the bottom plate to a top surface of the top plate.

According to an embodiment of the present disclosure, a thickness of the top plate and a thickness of the bottom plate are not less than 3.5 mm. According to a preferred embodiment of the present disclosure, the thickness of the bottom plate is 10 mm to 14 mm, and the thickness of the top plate is 2 mm to 6 mm.

According to an embodiment of the present disclosure, a diameter of the shielding through hole is 3 mm to 6 mm. According to a preferred embodiment of the present disclosure, the diameter of the shielding through hole is 4.5 mm.

On this basis, the present disclosure further proposes a detector. According to embodiments of the present disclosure, the detector includes the aforementioned collimator. Therefore, the detection efficiency and spatial resolution of the detector is high, and the quality of reconstructed images is good. Among them, it should be noted that the detector has all the technical features and technical effects of the aforementioned collimator, which will not be repeated herein.

According to an embodiment of the present disclosure, the detector is a variable-angle dual-detector SPECT imaging device.

Additional aspects and advantages of the present disclosure will be given in part in the following description, become apparent in part from the following description, or be learned from the practice of the present disclosure.

BRIEF DESCRIPTION OF THE DRAWINGS

The above and/or additional aspects and advantages of the present disclosure will become apparent and more readily appreciated from the following description of embodiments with reference to the drawings, in which.

DETAILED DESCRIPTION

Embodiments of the present application will be described in detail below, and the examples of the embodiments will be illustrated in the drawings. The same or similar elements and the elements having same or similar functions are denoted by like reference numerals throughout the description. The embodiments described herein with reference to the drawings are illustrative and used to generally explain the present disclosure. The embodiments shall not be constructed to limit the present disclosure.

In the description of the present disclosure, terms such as "longitudinal," "lateral," "upper," "lower," "front," "rear," "left," "right," "vertical," "horizontal," "top," "bottom" and the like should be constructed to refer to the orientation or position as then described or as shown in the drawings under discussion. These terms are for convenience of description and do not require that the present disclosure must be constructed and operated in a particular orientation, so these terms shall not be construed to limit the present disclosure.

It should be noted that terms such as "first" and "second" are used herein for purposes of description and are not intended to indicate or imply relative importance or to imply the number of indicated technical features. Thus, the feature defined with "first" and "second" may explicitly or implicitly comprise one or more of this feature. Further, in the description of the present disclosure, the term "a plurality of" means two or more than two, unless specified otherwise.

Collimator

According to an aspect of the present disclosure, a collimator for a detector is provided. The collimator according to embodiments of the present disclosure can reduce the overlap between different pinhole projections by using a top plate to secondarily shield radioactive rays passing through imaging through holes, and can change a ratio of a light-shielding rate by adjusting a distance between the top plate and a bottom plate and parameters of an imaging through hole and a shielding through hole. Hence, the detection efficiency and spatial resolution of an imaging system of the detector can be improved significantly, and better quality of reconstructed images can be achieved. Additionally, the collimator has low processing cost and can be popularized and applied widely.

In order to facilitate the understanding of the collimator, the collimator according to the embodiments of the present disclosure will be explained with reference to FIGS. 1-9. The collimator may include a bottom plate 100, a shielding case 200, and a top plate 300. The components of the collimator will be described in detail below.

Bottom Plate 100

Figure 1:
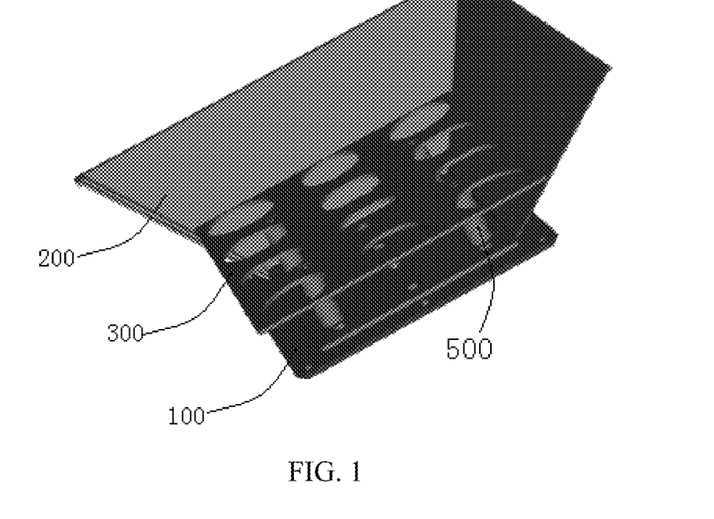
FIG. 1 is a partial schematic view of a collimator according to an embodiment of the present disclosure.
Figure 2:
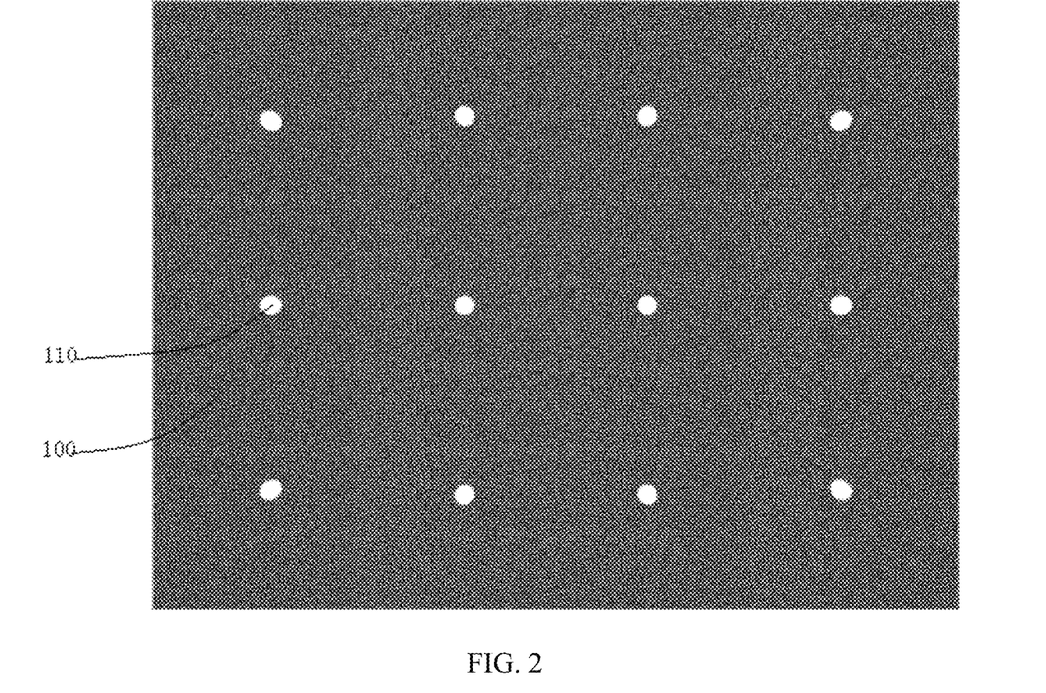
FIG. 2 is a schematic view of a bottom plate according to an embodiment of the present disclosure.
Figure 3:
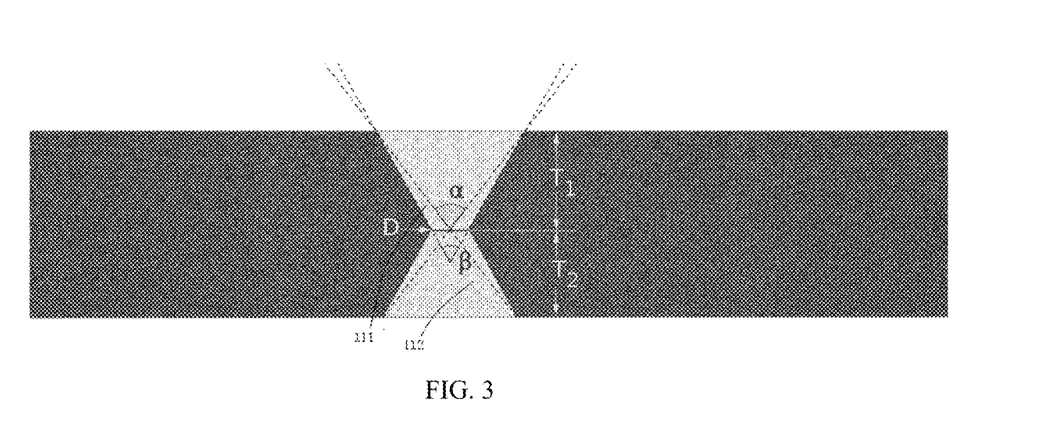
FIG. 3 is a schematic view of a longitudinal section of a bottom plate according to an embodiment of the present disclosure.

As shown in FIGS. 2 and 3, according to an embodiment of the present disclosure, the bottom plate 100 is provided with imaging through holes 110 distributed in an array. The imaging through hole 110 includes a first hole segment 111 and a second hole segment 112. A transverse size of the first hole segment 111 gradually decreases from a free end to the second hole segment, and a transverse size of the second hole segment 112 gradually decreases from a free end to the first hole segment 111. In other words, the transverse sizes of the first hole segment 111 and the second hole segment 112 gradually decrease from respective free ends to the center of the bottom plate. The inventors have found that compared with a single through hole segment, two through hole segments of the imaging through hole 110 according to the embodiment of the present disclosure can increase the material thickness at a position where the transverse size is the smallest, and reduce the intensity of rays penetrating this section.

The first hole segment 111 and the second hole segment 112 may be symmetrical or asymmetrical. In other words, the shape, height, transverse size, and other parameters of the first hole segment 111 and the second hole segment 112 may be identical or different. According to a preferred embodiment of the present disclosure, the first hole segment 111 and the second hole segment 112 are symmetrically arranged in an up-down direction.

According to an embodiment of the present disclosure, orientations (that is, directions of cone axes) of different imaging through holes 110 point to different directions, and all the orientations converge in a center of an imaging field of view. In this way, the different imaging through holes can image the same imaging field of view, and projections of an object to be imaged at different angles can be obtained simultaneously and used for reconstruction.

According to an embodiment of the present disclosure, the first hole segment 111 and the second hole segment 112 may independently be a truncated cone or a truncated polygonal pyramid. In other words, the first hole segment 111 and the second hole segment 112 can arbitrarily be a truncated cone or a truncated polygonal pyramid. Upper and lower surfaces of the truncated cone can be circular, elliptical, or other irregular circular shapes.

Shielding Case 200

According to an embodiment of the present disclosure, the shielding case 200 is formed on the bottom plate 100. As a result, the shielding case blocks light from entering the collimator from the external environment.

Top Plate 300

Figure 4:
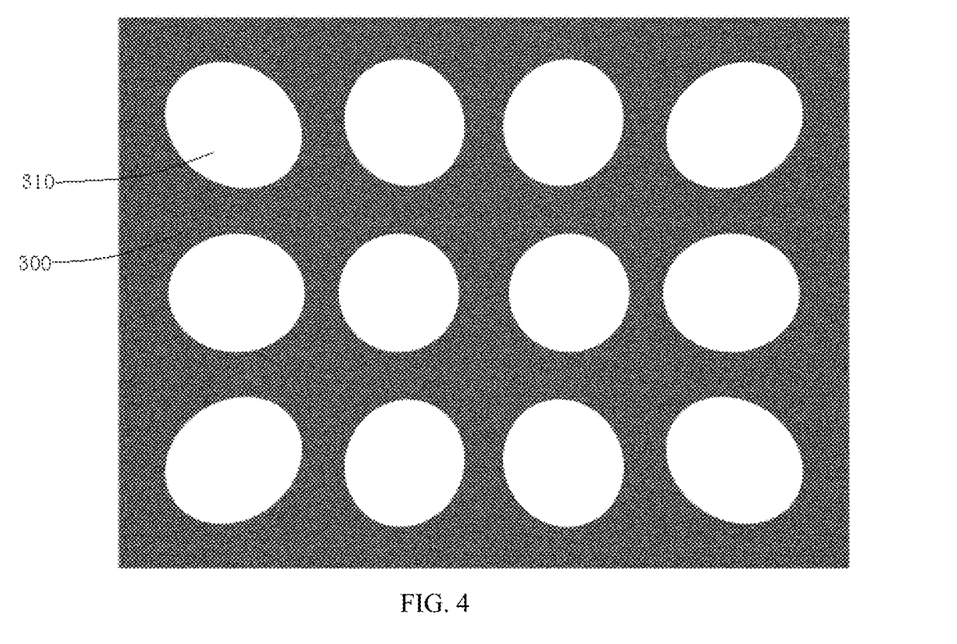
FIG. 4 is a schematic view of a top plate according to an embodiment of the present disclosure.

Referring to FIG. 4, according to an embodiment of the present disclosure, the top plate 300 is disposed in the shielding case 200 and closes at least a part of an opening of the shielding case 200. The top plate 300 is provided with shielding through holes 310 distributed in an array, and the imaging through holes 110 and the shielding through holes 310 are arranged in one-to-one correspondence. In other words, the top plate 300 is disposed relatively above the bottom plate 100 and a periphery of the top plate 300 is located in the shielding case 200. Thus, the radioactive rays passing through the imaging through holes can be secondarily shielded by the top plate, and the overlap between different pinhole projections can be reduced effectively; moreover, the ratio of the light-shielding rate can be changed by adjusting the distance between the top plate and the bottom plate and parameters of the imaging through holes and the shielding through holes. Hence, the detection efficiency and spatial resolution of the detector can be improved significantly, and the better quality of reconstructed images can be achieved.

According to an embodiment of the present disclosure, the bottom plate 100 and the top plate 300 are arranged in parallel. Thus, the structural design can be simplified and the assembly can be facilitated.

The light-shielding principle of the collimator will be further explained herein. As shown in FIG. 3, a target field of view is generally within a region covered by an opening angle α of a pinhole, but an angle in which incident radioactive rays can be actually received is β, wherein when an orientation of the pinhole is perpendicular to the bottom plate, the relationship between a and 13 is as follows:

$$\beta = 2\arctan\left(\tan\frac{\alpha}{2} + \frac{D}{T_0}\right) \quad (1)$$

in which:

α represents an included angle from a midpoint of a connecting surface of the first hole segment and the second hole segment to the free end of the first hole segment;

β represents an included angle between diagonals of the imaging through hole 110;

$T_0$ represents a thickness of the bottom plate 100, that is, $T_0=T_1+T_2$;

D represents a maximum radial dimension of the connecting surface of the first hole segment and the second hole segment.

Figure 5:
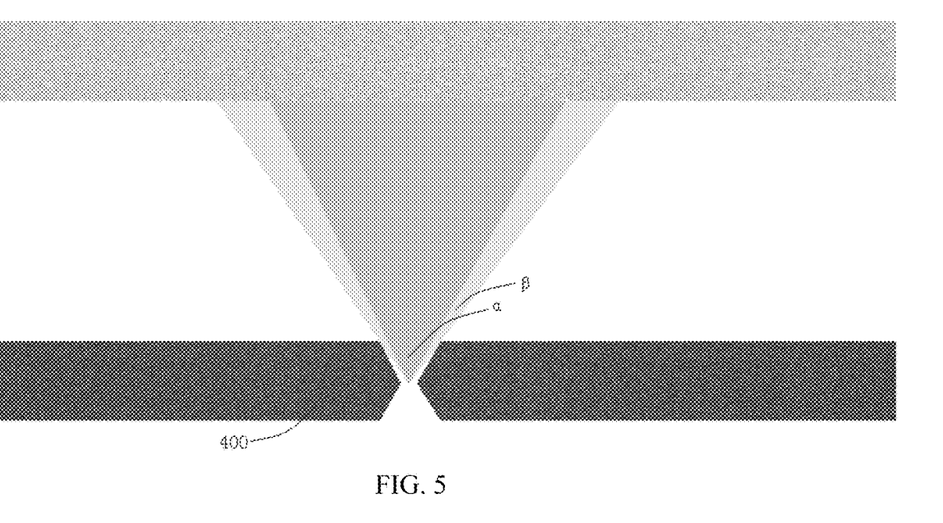
FIG. 5 is a schematic diagram showing a light-shielding principle of an existing collimator.

Respective projection ranges of an umbra region and a penumbra region are shown in FIG. 5. The umbra region refers to a projection region covered by the opening angle α in FIG. 5, and the penumbra region refers to a remaining region of a region covered by the opening angle β minus the umbra region as shown in FIG. 5. In this case, there are projections of both the umbra region and the penumbra region on a plane of the detector 600, and the shapes of the projections are circular. A projected area of the umbra region is denoted by $S_2$, and a projected area of the penumbra region is denoted by $S_1$. In a case of $T_1=0$, a ratio of $S_1$ to $S_2$ satisfies the following relationship:

$$\text{Light-shielding rate} = \frac{S_1}{S_2} = \left(\frac{H\tan\frac{\alpha}{2} + \frac{HD}{T} - \frac{D}{2}}{H\tan\frac{\alpha}{2} + \frac{D}{2}}\right)^2 - 1 \quad (2)$$

in which:

$S_1$ represents the projected area of the penumbra region of the collimator, that is, an area of the remaining region of the region covered by the opening angle β minus the umbra region as shown in FIG. 5;

$S_2$ represents the projected area of the umbra region of the collimator, that is, an area of the projection region covered by the opening angle α in FIG. 5;

H represents a distance from a center of the imaging through hole 110 to a surface of the detector;

α represents the included angle from the midpoint of the connecting surface of the first hole segment and the second hole segment to the free end of the first hole segment 111;

D represents a maximum diameter of the imaging through hole 110;

T represents a distance from a bottom surface of the bottom plate 100 to a top surface of the top plate 300.

Figure 6:
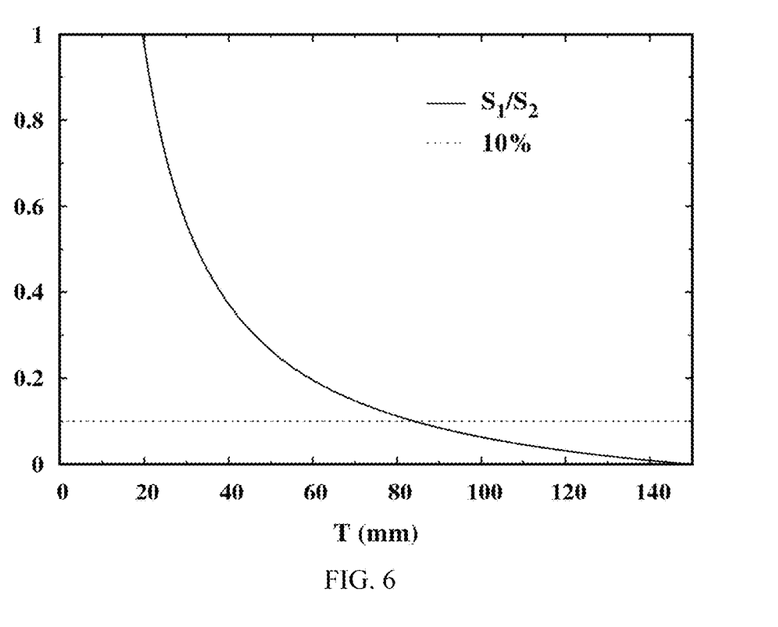
FIG. 6 is a schematic diagram showing a result of a light-shielding rate according to an embodiment of the present disclosure.

Among them, the light-shielding rate is the ratio of the projected area $S_1$ of the penumbra region to the projected area $S_2$ of the umbra region, and the relationship between the light-shielding rate and the thickness of the collimator is shown in FIG. 6. It can be seen from FIG. 6 that in order to reduce the area of the penumbra region to about 10% of the area of the umbra region, that is, the light-shielding rate is 10%, the thickness of the collimator must be at least about 80 mm. Generally, the materials used to manufacture collimators are expensive, and some materials (e.g., tungsten) are difficult to process, so it is impractical to adopt a thick collimator. The inventors have found in the research that by providing the top plate 300 for secondary shielding, the bottom plate 100 and the top plate 300 jointly realize the function of a light-shielding plate 400 in FIG. 5, that is, the bottom plate 100, the top plate 300, and a part between the two together form the light-shielding plate 400 in FIG. 5, such that the thicknesses of the bottom plate 100 and the top plate 300, and the distance between the bottom plate 100 and the top plate 300 can be significantly reduced, and imaging through holes 110 and shielding through holes 310 of different shapes and sizes can be realized to meet different design requirements and render great flexibility.

In an embodiment of the present disclosure, as shown in FIG. 4, there are twelve elliptical shielding through holes 310 in the top plate 300 and in one-to-one correspondence with the imaging through holes 110 in the bottom plate.

Figure 7:
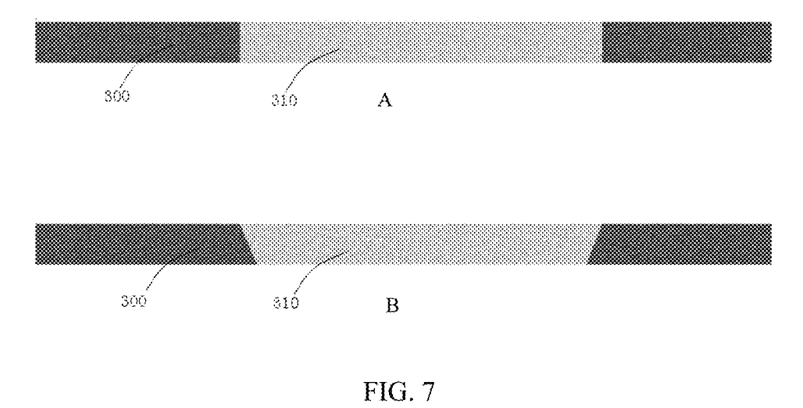
FIG. 7 is a schematic view of a longitudinal section of a top plate according to an embodiment of the present disclosure.

As shown in FIG. 7, according to an embodiment of the present disclosure, the shielding through hole 310 is a straight hole (as shown in FIG. 7A) or an oblique hole (as shown in FIG. 7B). If the oblique hole is changed into the straight hole, the processing will be facilitated and the influence on the shielding effect can be ignored, so those skilled in the art can make a choice in the light of the processing difficulty.

Figure 8:
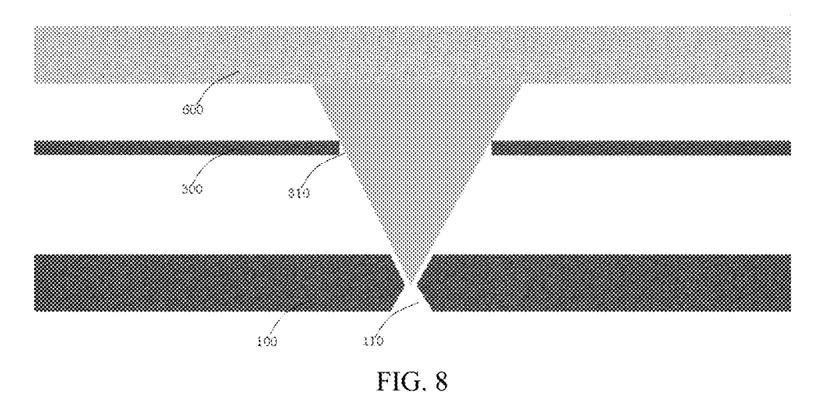
FIG. 8 is a schematic diagram showing a light-shielding principle of a collimator according to an embodiment of the present disclosure.
Figure 9:
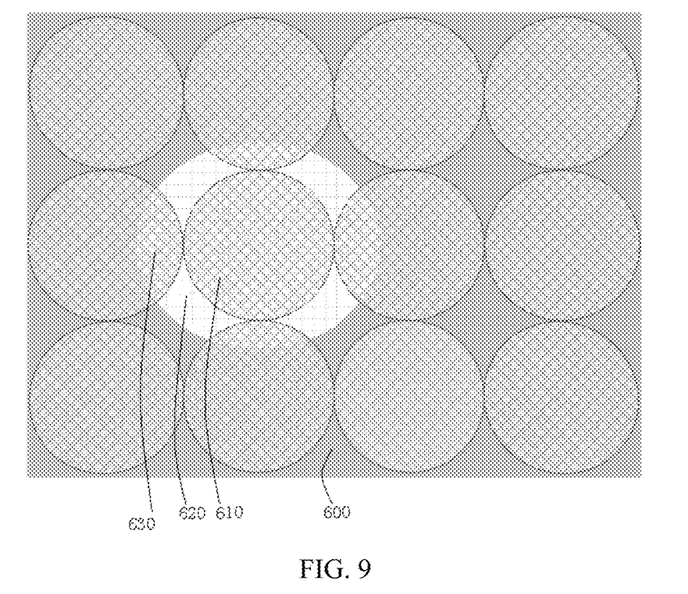
FIG. 9 is a schematic diagram showing a light-shielding result of a collimator according to an embodiment of the present disclosure.
Figure 10:
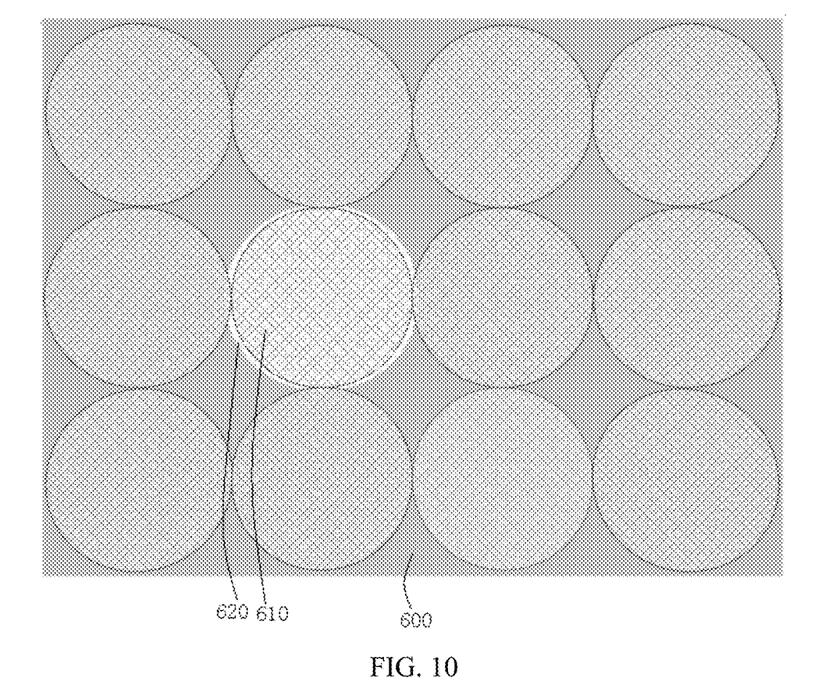
FIG. 10 is a schematic diagram showing a light-shielding result of a collimator according to an embodiment of the present disclosure.

Further, the size of the elliptical hole is designed to shield the projection of the penumbra region of the imaging pinhole as much as possible without affecting the projection of the umbra region. The shielding effect is as shown in FIGS. 8, 9 and 10. In FIG. 10, the penumbra region on the imaging detector is very small, and hardly overlaps with the umbra region adjacent thereto. The inventors have found that when a lower edge of the shielding through hole 310 coincides with an intersection line between an extension surface of a peripheral surface where an inner wall of the first hole segment 111 is located and a lower surface of the top plate 300, that is, when a pattern formed by the intersection between the extension surface of the peripheral surface where the inner wall of the first hole segment 111 is located and the lower surface of the top plate 300 constitutes the lower edge of the shielding through hole 310, the light-shielding rate is small and the area $S_1$ of the penumbra region is close to zero.

Additionally, it should be noted that the distance between the bottom plate 100 and the top plate 300, as well as the imaging through holes 110 and shielding through holes 310 of different shapes and sizes, can be adjusted flexibly according to different design requirements. As a result, additional projections of rays from non-target organs at certain angles can be selectively shielded, to block out unwanted data or other data diminishing the image quality, so as to improve the detection efficiency and spatial resolution of the detector significantly and enjoy the better quality of reconstructed images.

As described above, compared with the existing collimator, the equivalent thickness of the collimator according to the embodiments of the present disclosure is the distance from the bottom surface of the bottom plate 100 to the top surface of the top plate 300, which is equivalent to a sum of the thickness of the bottom plate 100, the thickness of the top plate 300, and the distance between the bottom plate 100 and the top plate 300. After D is calculated according to formula (2) and the set value of the light-shielding rate S1/S2, the distance between the two plates can be determined by subtracting the thickness of the bottom plate and the thickness of the top plate from T.

In an embodiment of the present disclosure, the bottom plate 100, the top plate 300, and the shielding case 200 may be made of at least one of gold, tantalum, platinum, tungsten, and lead.

Further, in a preferred embodiment of the present disclosure, the bottom plate 100, the top plate 300, and the shielding case 200 may be made of the same material.

It should be noted herein that the thicknesses of the bottom plate 100 and the top plate 300 need to guarantee that they will not be penetrated by rays. If the energy of rays is 140 keV, the material for the plates is tungsten, and the plates are set to shield at least 99.999% of the rays, a minimum thickness T of each plate can be calculated using the following formula:

$$T_{min} = \frac{-\log(1 - 99.999\%)}{\mu} = 3.5 \text{mm} \quad (3)$$

wherein $\mu=3.268$ mm$^{-1}$, which is a linear attenuation coefficient of the material tungsten for photons with the energy of 140 keV.

Accordingly, in an embodiment of the present disclosure, the thickness of the top plate 300 and that of the bottom plate 100 are not less than 3.5 mm. As a result, the rays can be effectively shielded and be prevented from penetrating the two plates.

Meanwhile, in order to ensure that the rays passing through one imaging through hole 110 can only reach one corresponding shielding through hole 310, the thickness of the bottom plate cannot be too small. According to a preferred embodiment of the present disclosure, the thickness of the bottom plate 100 is 10 mm to 14 mm, and the thickness of the top plate 300 is 2 mm to 6 mm. Therefore, the thicknesses of the bottom plate and the top plate are appropriate, and the rays of the imaging through hole can only reach the corresponding shielding through hole, such that the light-shielding rate is lower, the detection efficiency and spatial resolution of the detector can be significantly improved, and the better quality of reconstructed images can be achieved.

Specifically, according to a preferred embodiment of the present disclosure, the diameter of the shielding through hole 310 is 3 mm to 6 mm. According to a preferred embodiment of the present disclosure, the diameter of the shielding through hole 310 is 4.5 mm. Therefore, the diameter of the shielding through hole is appropriate, such that the rays of the imaging through hole can only reach the corresponding shielding through hole, and the light-shielding rate can become lower.

According to an embodiment of the present disclosure, the collimator further includes a supporting member 500 arranged between the top plate 300 and the bottom plate 100 and used to support and fix the top plate 300 and the bottom plate 100.

According to an embodiment of the present disclosure, the supporting member 500 may also be made of at least one of tungsten, lead, gold, platinum, and tantalum. Further, the supporting member 500 can also be made of the same material as the top plate 300 and the bottom plate 100.

Detector

On this basis, the present disclosure further proposes a detector. According to embodiments of the present disclosure, the detector includes the aforementioned collimator. Therefore, the detection efficiency and spatial resolution of the detector is high, and the quality of reconstructed images is good. According to the embodiments of the present disclosure, the dual-detector SPECT equipped with the aforementioned collimator can perform tomographic imaging and dynamic tomographic imaging of small human organs without rotation. Among them, it should be noted that the detector has all the technical features and technical effects of the aforementioned collimator, which will not be repeated herein.

Additionally, it should be noted that the detector according to the embodiments of the present disclosure is particularly suitable for imaging small human organs such as heart, thyroid, or brain, but the use of the detector is not limited to tomographic imaging and dynamic tomographic imaging of small human organs. It is also possible to perform tomographic imaging and dynamic tomographic imaging for some organs and viscera of animals, as well as other targets that can be imaged by the detector according to the embodiments of the present disclosure, all of which are applicable to the detector according to the embodiments of the present disclosure.

Figure 11:
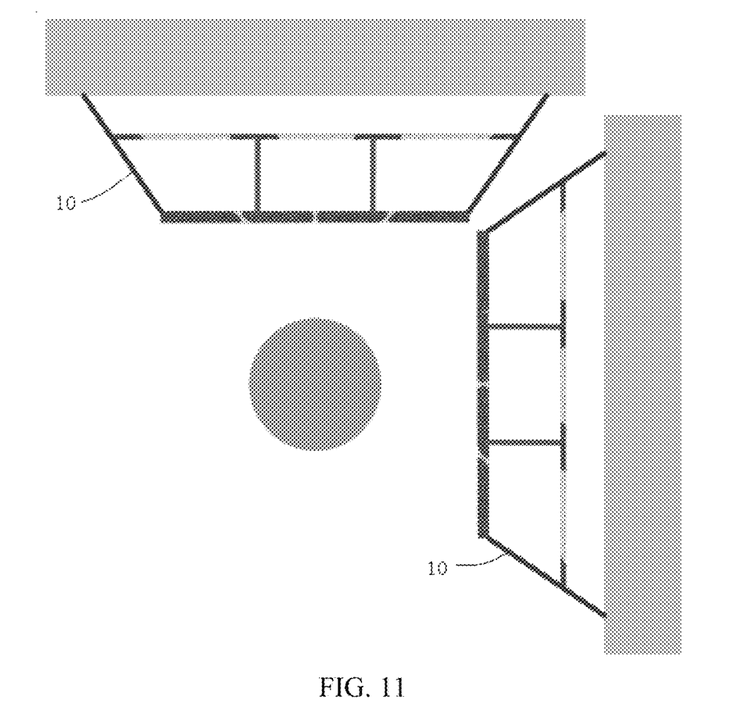
FIG. 11 is a schematic diagram showing dual-detector SPECT imaging according to an embodiment of the present disclosure.

According to an embodiment of the present disclosure, the detector is a variable-angle dual-detector SPECT imaging device. As shown in FIG. 11, it is a schematic diagram of imaging a human organ by a dual-detector SPECT. In a multi-pinhole SPECT imaging device with the aforementioned collimator 10, the two detectors are arranged at a certain angle, the imaging field of view is located between the included angle of the two detectors, and all the pinholes can cover a spherical field of view that is sufficient to enclose a heart region. As a result, the SPECT imaging device can achieve high sensitivity, and for example, rapid tomographic imaging of the heart can be achieved without rotation, and in particular, the device can also achieve dynamic imaging of the heart.

In the description of the present specification, reference throughout this specification to "an embodiment," "some embodiments," "an example," "a specific example," or "some examples" means that a particular feature, structure, material, or characteristic described in connection with the embodiment or example is included in at least one embodiment or example of the present disclosure. In the specification, the appearances of the above-mentioned terms are not necessarily referring to the same embodiment or example of the present disclosure. Furthermore, the particular features, structures, materials, or characteristics may be combined in any suitable manner in one or more embodiments or examples.

Although embodiments of the present disclosure have been shown and described, it shall be appreciated by those skilled in the art that various changes, modifications, alternatives, and variations can be made in the embodiments without departing from principles and purposes of the present disclosure. The scope of the present disclosure is defined by claims or their equivalents.

What is claimed is:

1. A collimator for a detector, comprising:
    a bottom plate provided with imaging through holes distributed in an array, wherein the imaging through hole comprises a first hole segment and a second hole segment, wherein a transverse size of the first hole segment gradually decreases from a free end to the second hole segment, and a transverse size of the second hole segment gradually decreases from a free end to the first hole segment;
    a shielding case formed on the bottom plate and blocking light from entering the collimator from the external environment;
    a top plate arranged in the shielding case and closing at least a part of an opening of the shielding case, wherein the top plate is provided with shielding through holes distributed in an array, and the imaging through holes and the shielding through holes are arranged in one-to-one correspondence; and
    a supporting member arranged between the top plate and the bottom plate and configured to support and fix the top plate and the bottom plate,
    wherein the shielding case surrounds the bottom plate and the top plate, and a periphery of the top plate is within the shielding case.

2. The collimator according to claim 1, wherein the first hole segment and the second hole segment are symmetrically arranged in an up-down direction.

3. The collimator according to claim 1, wherein the first hole segment and the second hole segment are independently configured into a truncated cone or a truncated polygonal pyramid.

4. The collimator according to claim 1, wherein the shielding through hole is a straight hole or an oblique hole.

5. The collimator according to claim 1, wherein a lower edge of the shielding through hole coincides with an intersection line between an extension surface of a peripheral surface where an inner wall of the first hole segment is located and a lower surface of the top plate.

6. The collimator according to claim 1, wherein the collimator has a light-shielding rate of less than 10%, wherein the light-shielding rate is determined by the formula:

$$\text{Light-shielding rate} = \frac{S_1}{S_2} = \left( \frac{H \tan\frac{\alpha}{2} + \frac{HD}{T} - \frac{D}{2}}{H \tan\frac{\alpha}{2} + \frac{D}{2}} \right)^2 - 1$$

in which:
   $S_1$ represents a projected area of a penumbra region of the collimator;
   $S_2$ represents a projected area of an umbra region of the collimator;
   H represents a distance from a center of the imaging through hole to a surface of the detector;
   $\alpha$ represents an included angle from a midpoint of a connecting surface of the first hole segment and the second hole segment to the free end of the first hole segment;
   D represents a maximum diameter of the imaging through hole;
   T represents a distance from a bottom surface of the bottom plate to a top surface of the top plate.

7. The collimator according to claim 1, wherein a thickness of the top plate and a thickness of the bottom plate are not less than 3.5 mm.

8. The collimator according to claim 1, wherein a thickness of the bottom plate is 10 mm to 14 mm, and a thickness of the top plate is 2 mm to 6 mm.

9. The collimator according to claim 1, wherein a diameter of the shielding through hole is 3 mm to 6 mm.

10. The collimator according to claim 1, wherein a diameter of the shielding through hole is 4.5 mm.

11. A detector, comprising a collimator, wherein the collimator comprises:
- a bottom plate provided with imaging through holes distributed in an array, wherein the imaging through hole comprises a first hole segment and a second hole segment, wherein a transverse size of the first hole segment gradually decreases from a free end to the second hole segment, and a transverse size of the second hole segment gradually decreases from a free end to the first hole segment;
- a shielding case formed on the bottom plate and blocking light from entering the collimator from the external environment;
- a top plate arranged in the shielding case and closing at least a part of an opening of the shielding case, wherein the top plate is provided with shielding through holes distributed in an array, and the imaging through holes and the shielding through holes are arranged in one-to-one correspondence; and
- a supporting member arranged between the top plate and the bottom plate and configured to support and fix the top plate and the bottom plate,
- wherein the shielding case surrounds the bottom plate and the top plate, and a periphery of the top plate is within the shielding case.

12. The detector according to claim 11, wherein the detector is a variable-angle dual-detector single photon emission computed tomography imaging device.

13. The detector according to claim 11, wherein orientations of different imaging through holes point to different directions and converge in a center of an imaging field of view.

14. The detector according to claim 11, wherein the first hole segment and the second hole segment are symmetrically arranged in an up-down direction.

15. The detector according to claim 11, wherein the first hole segment and the second hole segment are independently configured into a truncated cone or a truncated polygonal pyramid.

16. The detector according to claim 11, wherein the shielding through hole is a straight hole or an oblique hole.

17. The detector according to claim 11, wherein a lower edge of the shielding through hole coincides with an intersection line between an extension surface of a peripheral surface where an inner wall of the first hole segment is located and a lower surface of the top plate.

18. The detector according to claim 11, wherein the collimator has a light-shielding rate of less than 10%, wherein the light-shielding rate is determined by the formula:

$$\text{Light-shielding rate} = \frac{S_1}{S_2} = \left(\frac{H\tan\frac{\alpha}{2} + \frac{HD}{T} - \frac{D}{2}}{H\tan\frac{\alpha}{2} + \frac{D}{2}}\right)^2 - 1$$

in which:
- $S_1$ represents a projected area of a penumbra region of the collimator;
- $S_2$ represents a projected area of an umbra region of the collimator;
- H represents a distance from a center of the imaging through hole to a surface of the detector;
- α represents an included angle from a midpoint of a connecting surface of the first hole segment and the second hole segment to the free end of the first hole segment;
- D represents a maximum diameter of the imaging through hole;
- T represents a distance from a bottom surface of the bottom plate to a top surface of the top plate.

19. The detector according to claim 11, wherein the bottom plate, the top plate, the shielding case, and the supporting member may be made of at least one of gold, tantalum, platinum, tungsten, and lead.

* * * * *